US006596480B1

(12) United States Patent
Didenko et al.

(10) Patent No.: US 6,596,480 B1
(45) Date of Patent: *Jul. 22, 2003

(54) ASSAY FOR DETECTING APOPTOTIC CELLS

(75) Inventors: Vladimir Didenko, Houston, TX (US); Peter Hornsby, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/308,324
(22) PCT Filed: Nov. 26, 1997
(86) PCT No.: PCT/US97/21271
§ 371 (c)(1),
(2), (4) Date: Nov. 6, 2000
(87) PCT Pub. No.: WO98/23777
PCT Pub. Date: Jun. 4, 1998

(51) Int. Cl.[7] .............................. C12Q 1/68; C12Q 1/66; C12Q 1/28; C12Q 1/42; G01N 33/53; C07H 21/02; C07H 21/04
(52) U.S. Cl. ............................ 435/6; 435/7.1; 435/8; 435/21; 435/28; 536/23.1; 536/24.3
(58) Field of Search ............................. 435/6, 7.1, 8, 1, 435/28; 536/23.1, 24.3

(56) References Cited

U.S. PATENT DOCUMENTS

| | | | |
|---|---|---|---|
| 5,330,972 A | | 7/1994 | Cope |
| 5,484,710 A | | 1/1996 | Reed et al. |
| 5,500,432 A | | 3/1996 | Nicolaou et al. |
| 5,512,435 A | | 4/1996 | Renschler et al. |
| 5,527,682 A | | 6/1996 | Ownes et al. |
| 5,624,808 A | | 4/1997 | Thompson et al. |
| 6,013,438 A | * | 1/2000 | Didenko et al. .......... 435/6 |

OTHER PUBLICATIONS

Ansari B, et al.; In situ end–labelling detects DNA strand breaks in apoptosis and other physiological and pathological states; J pathol May 1993; 170(1):1–8.
Arends, et al., American Journal of Pathology 136(3), 593–608, 1990. Apoptosis: The role of the Endonuclease.
Columbano, A., Journal of Cellular Biochemistry 58, 181–190, 1995. Cell Death: Current Difficulties in Discriminating Apoptosis from Necrosis in the Context of Pathological Processes In Vivo.
Didenko, et al., Journal of Clinical Investigation 97(7), 1723–1731, 1996. Expression of $p21^{WAF1/CIP1/SDI1}$ and p53 in Apoptotic Cells in the Adrenal Cortex and Induction by Ischemia/Reperfusion Injury.
Didenko, et al., Journal of Histochemistry and Cytochemistry 44(6), 657–660, 1996. A Quantitative Luminescence Assay for Nonradioactive Nucleic Acid Probes.
Gavrieli, et al., Journal of Cell Biology 119(3), 493–502, 1992. Identifiaction of Programmed Cell Death In Situ via Specific Labelling of Nuclear DNA Fragmentation.
Grasil–Kraupp, et al., Hepatology 21, 1465–1468, 1995, In situ Detection of Fragmented DNA (TUNEL Assay) Fails to Discriminate Among Apoptosis, Necrosis and Autolytic Cell death: A Cautionary Note.
Lutter, Nucleic Acids Research 6(1) 41–56, 1979. Precise location of DNase I cutting sites in the nucleosome core determined by high resolution gel electrophoresis.
Sasano, H., Endocrine Pathology 6(2), 87–89, 1995. In Situ End Labeling and Its Applications to the Study of Endocrine DIsease: How Can We Study Programmed Cell Death in Surgical Pathology Materials.
Sollner–Webb, et al., Cell 14, 611–627, 1978. DNase I, DNase II and Staphylococcal Nuclease Cut at Different, Yet Symmetrically Located, Sites in the Nucleosome Core.
Van Lookeren Campagne, et al., European Journal of Neuroscience 7, 1627–1640, 1995. NMDA and Kainate Induce Internucleosomal DNA Cleavage Associated with Both Apoptotic and Necrotic Cell Death in the Neonatal Rat Brian.
Yang, et al., Experimental Cell Research 221, 126–131, 1995. Increased experssion of $p21^{Sdi1}$ in Adrenocortical Cells When They are Placed in Culture.
Yasuda, M., et al., Archives of Histology and Cytology 58(2), 185–190, 1995. Apoptotic Cells in the Human Endometrium and Placental Villi: Pitfalls in Applying the TUNEL Method.

* cited by examiner

Primary Examiner—Kenneth R. Horlick
Assistant Examiner—Teresa Strzelecka
(74) Attorney, Agent, or Firm—Fulbright & Jaworski, L.L.P.

(57) ABSTRACT

The invention relates to the detection of apoptotic cells using a novel assay that employs ligation of DNA fragments in situ to selectively label apoptotic cells. The assay may be used in combination with known in situ methodologies to simultaneously detect apoptotic cells and specific biomolecules present in the apoptotic cell.

33 Claims, 5 Drawing Sheets

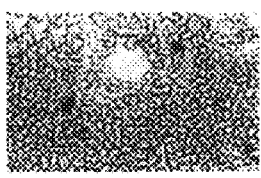
FIG. 3(a)
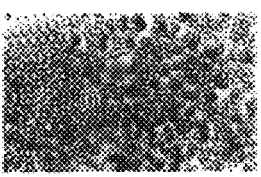
FIG. 3(a')
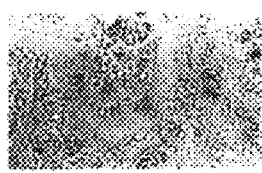
FIG. 3(d)
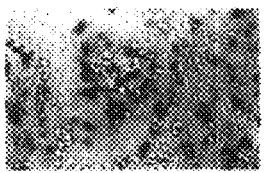
FIG. 3(d')
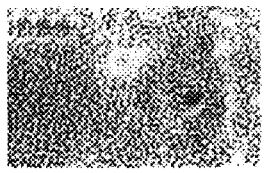
FIG. 3(b)
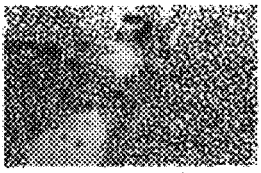
FIG. 3(b')
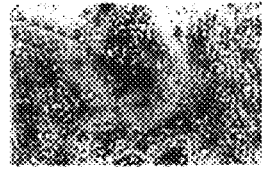
FIG. 3(e)
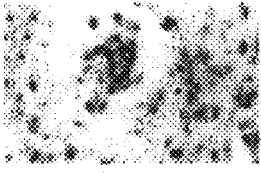
FIG. 3(e')
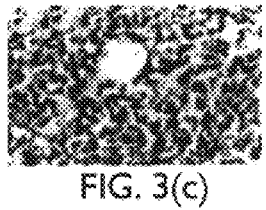
FIG. 3(c)
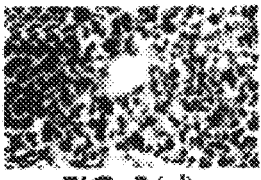
FIG. 3(c')
FIG. 3(f)
FIG. 3(f')

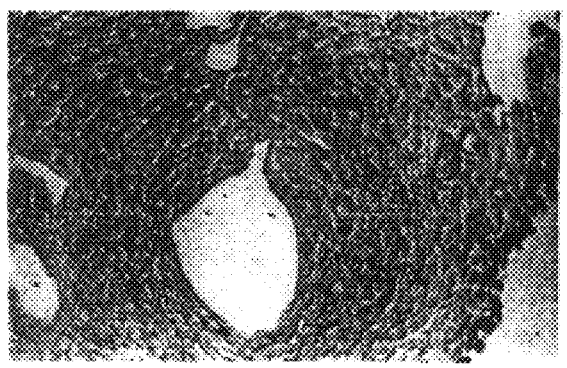
FIG. 5(a)
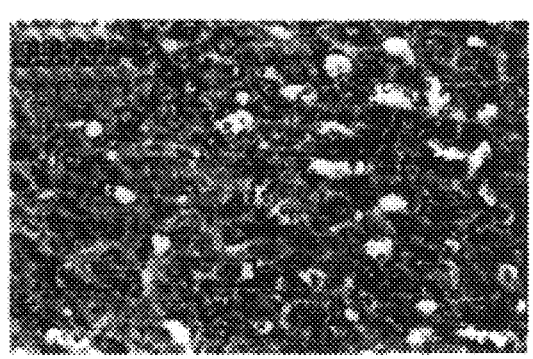
FIG. 7(a)
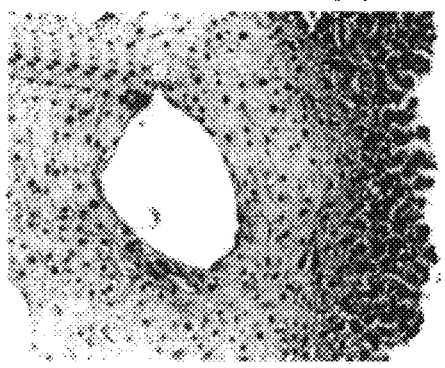
FIG. 5(b)
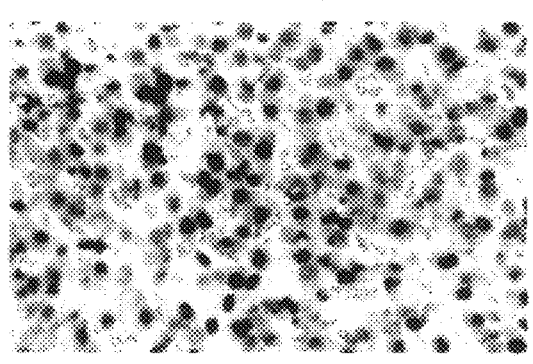
FIG. 7(b)
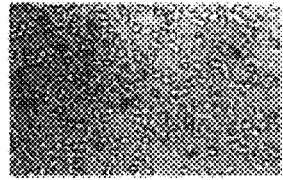
FIG. 6(a)
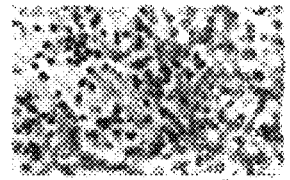
FIG. 6(a')
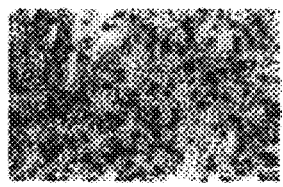
FIG. 6(b)
FIG. 6(b')
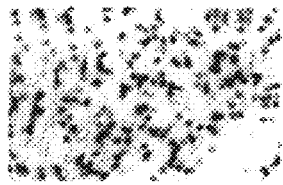
FIG. 6(c)
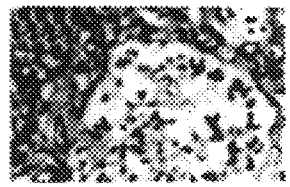
FIG. 6(c')

SEQUENCE LISTING

```
<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
gtggcctgcc caagctctac ct                                              22

<210> SEQ ID NO 2
<211> LENGTH: 28
<212> TYPE: DNA
<213> ORGANISM: Artificial Sequence
<220> FEATURE:
<223> OTHER INFORMATION: Primer

<400> SEQUENCE: 2
ggctggtctg ccgccgtttt cgaccctg                                        28

<210> SEQ ID NO 3
<211> LENGTH: 41
<212> TYPE: DNA
<213> ORGANISM: Artificial Sequence
<220> FEATURE:
<223> OTHER INFORMATION: Hairpin Oligonucleotide
<220> FEATURE:
<221> NAME/KEY: misc_feature
```

-continued

```
<222> LOCATION: (1)..(41)
<223> OTHER INFORMATION: N equals C6-deoxyuridine

<400> SEQUENCE: 3
gcgctagacc gatcnaganc tnatgnagan ggtctagcgc a                    41
```

ASSAY FOR DETECTING APOPTOTIC CELLS

This application is a 371 of PCT/US97/21271, filed on Nov. 26, 1997, which claims priority to application Ser. No. 08/758,027, filed on Nov. 27, 1996, now U.S. Pat. No. 6,013,438.

FIELD OF THE INVENTION

This invention relates generally to the fields of molecular biology and cell biology and, more specifically, to apoptosis and methods for detecting apoptosis in biological samples.

BACKGROUND OF THE INVENTION

Apoptosis is a process of programmed cell death by which multicellular organisms selectively delete cells. The term necrosis is used to describe the morphological changes undergone by cells that die by processes other than apoptosis. Apoptosis is characterized by a progressive condensation of the chromatin to the inner face of the nuclear membrane, cell shrinkage with consequent loss of membrane contact with neighboring cells, and fragmentation of the cells with formation of membrane-bound acidophilic globules (apoptotic bodies).

The DNA of cells that have undergone apoptosis is cleaved into fragments that are multiples of approximately 180 base pairs. These fragments can be seen after agarose gel electrophoresis as a characteristic "ladder" develops. This ladder is widely used as a biochemical marker for discriminating apoptotic cell death from necrotic cell death as the DNA of necrotic cells is randomly degraded and does not produce a ladder. The ladder develops as a result of cleavage of nuclear DNA within the linker regions between nucleosomes. Double strand cleavage results from frequent nicks on both DNA strands.

Although the endonuclease responsible for the cleavage of DNA in apoptotic cells has not been definitively identified, candidate nucleases with properties consistent with their involvement in apoptosis have been identified in apoptotic cells.

The endonucleases that have been identified in apoptotic cells are generally similar in their properties to pancreatic DNase I. Specifically, these endonucleases share the following characteristics:

(i) the DNA ends produced by DNase I cleavage (5'-phosphate and 3'-hydroxyl) are the same as those found in apoptotic nuclei;

(ii) DNase I-transfected COS cells show chromatin changes similar to those seen in apoptosis; and (iii) DNase I cleavage of chromatin produces the same characteristic nucleosomal DNA fragments that can be isolated from apoptotic cells.

Although DNase I has been detected in cells undergoing apoptosis and the tissue distribution of DNase I is consistent with a role in apoptosis, the endonucleases partially purified from apoptotic cells were shown to be distinct from DNase I. There is less evidence for the involvement of DNase II and other endonucleases in apoptosis.

Presently, the terminal deoxynucleotidyl transferase (TdT)-mediated biotinylated dUTP nick end labeling (TUNEL) method is used to detect apoptotic cells in tissue sections. The TUNEL method utilizes TdT to incorporate a biotinylated deoxyuridine label into DNA fragments containing a 3'-hydroxyl group. The label can be detected using a variety of avidin/streptavidin based detection methodologies. Although 3'-hydroxyl groups are present in the double stranded DNA breaks in the apoptotic cells, they are also present in the DNA of cells that have undergone necrotic cell death. This method, therefore, is not suitable for distinguishing between necrotic cell death and apoptotic cell death. In addition, this methodology does not permit the simultaneous detection of 3'-hydroxyl groups and other biologically relevant molecules, such as RNA and proteins.

Presently, there is a need in the art for a methodology to specifically detect apoptotic cells. There is presently no methodology that permits the specific detection of apoptotic cell death without the simultaneous detection of necrotic cells. In the experiments reported here, we determined whether DNA double strand breaks characteristic of those produced by an endonuclease like DNase I can be detected in apoptotic cells in situ.

When DNA is bound to histones or other proteins in chromatin, it is partially protected from the action of endonucleases, which are able to cleave the DNA at approximately 10-bp intervals, the distance of a single helical turn of the DNA. Because of the helical twist of DNA, the two strands are accessible to endonucleases with production of staggered ends as well as some blunt ends. Thus DNase I cleavage of nucleosome-bound DNA gives rise to double strand cuts with 1, 2, or 3 bases of 3' overhang.

In contrast, DNase II cleavage of DNA in chromatin yields longer 3'-overhangs of an average of 4 bases.

SUMMARY OF THE INVENTION

To detect double-stranded DNA ends in apoptotic nuclei in situ, we used several types of double-stranded, labeled DNA fragments which were ligated to DNA ends present in the nuclei of cells in sections of fixed paraffin-embedded tissues. To detect single-base 3'-overhangs, we took advantage of the fact that double-stranded DNA fragments synthesized by Taq DNA polymerase in the polymerase chain reaction have a single 3' base extension beyond the templated sequence. Although it was originally suggested that Taq polymerase added only deoxyadenosine to the 3'-ends of double-stranded DNA, other work subsequently established that if the last templated 3'-nucleotide synthesized is deoxycytidine, Taq polymerase will add deoxyadenosine or deoxycytidine, leaving no blunt-ended DNA, thus providing a fragment that could potentially ligate to the recessed 5'-base of many of the single-base 3'-overhangs in a random DNA sequence. To prepare a fragment that can be ligated only to blunt ends, PCR was performed using Pfu DNA polymerase, because this polymerase produces blunt-ended products only.

An alternative method of preparing DNA fragments for use as ligation probes is to synthesize oligonucleotides that form ends that can be ligated. Rather than using two complementary strands in the fashion customarily employed for the production of oligonucleotide linkers, a single oligonucleotide may be synthesized such that a region on the 3'-end of the oligonucleotide is complementary to a region on the 5'-end. When the complementary regions of the oligonucleotide anneal, a hairpin structure with a stem and loop spontaneously forms.

The stem structure formed has a double-stranded end that may be ligated to a compatible end. When the regions of complementarity include the 5'-most and 3'-most nucleotides, the stem formed has a blunt end. By adding nucleotides to either the 3'-end or the 5'-end without adding the complementary nucleotide to the other end of the oligonucleotide, an overhang can be created. By including the appropriate number of nucleotides on the desired end, a 3'-overhang or a 5'-overhang of any length can be created. Additionally, any desired sequence can be incorporated into the overhanging portion of the oligonucleotide.

Using the ligation procedure and probes described, we determined that apoptotic nuclei, but not nuclei in necrotic tissue or tissue with other non-apoptotic DNA damage, have DNA ends that can be ligated to labeled DNA fragments with single-base 3' overhangs. In addition, we found that DNA having ends characteristic of apoptosis could be detected with blunt ended DNA probes as well as with probes having two and three base 3'-overhangs.

In contrast, nuclei with all forms of DNA damage have a high concentration of 3'-hydroxyl DNA ends that are a substrate for terminal deoxynucleotidyl transferase (TdT). As TdT can extend the 3' base of single-stranded DNA and overhanging, blunt, and recessed 3' bases of double-stranded DNA, TdT based methodologies are not suitable to distinguish apoptotic cells from necrotic cells. In contrast, ligation based methodologies are suitable to accomplish this very desirable objective.

The present invention provides a methodology for specifically detecting the presence of apoptotic cells in tissue sections. The present invention overcomes the limitations of the prior art by employing a novel ligation methodology to detect DNA fragments that are diagnostic of apoptotic cells.

One aspect of the present invention includes a method for detecting apoptotic cells in tissue sections. This method uses a novel in situ ligation methodology to label double strand DNA breaks with overhanging termini diagnostic of apoptotic cells.

Another aspect of the present invention is to provide a method of detecting and isolating DNA fragments that have defined termini using a solid phase capture assay.

Another aspect of the invention includes a method for detecting the presence of apoptotic cells in a tissue sample using the ligation methodology presented herein in a DNA blot format. The DNA is isolated from the sample and fractionated by size using agarose gel electrophoresis. The DNA is then transferred to a solid support and probed using the ligation methodology. This method is more sensitive than currently available technologies and permits the detection of a small number of apoptotic cells when the apoptotic cells form only a small portion of the tissue sample.

Another aspect of the present invention is to provide a method for detecting the presence of biologically important macromolecules in a cell undergoing apoptosis. These macromolecules include proteins and RNA. This method permits the simultaneous detection of an apoptotic cell and the detection of the presence of specific macromolecules within the apoptotic cell.

Another aspect of the present invention is to provide a methodology for analyzing DNA to determine whether the DNA has been acted upon by a nuclease and, if the DNA has been acted upon by a nuclease, to determine what type of nuclease has acted upon the DNA.

Another aspect of the invention is to provide a method that allows the determination of the nature of DNA damage caused by the activity of nucleases upon the DNA and specific RNA synthesis associated with that damage.

BRIEF DESCRIPTION OF THE DRAWINGS

FIG. 1 illustrates detection of different types of DNA ends within apoptotic cells in rat thymus. FIGS. 1a', b', and c' are the reaction products of the 3' labeling methods using 6-fold longer times of alkaline phosphatase color development (90 and 42 minutes respectively).

FIG. 2 shows the comparison of patterns of apoptotic cells, detected by the presence of different types of DNA ends, in control and glucocorticoid treated rat thymus. Thymus from control (FIGS. 2a, 2b) and glucocorticoid-treated (FIGS. 2c, 2d) rats were fixed and processed as described in FIG. 1.

FIG. 3 shows the detection of DNA ends within necrotic cells in Wilms' tumor by three labeling methods. Serial sections were used and the same regions are shown by the three labeling methods. FIGS. 3a and 3d show the ligation of Taq polymerase fragment, 15 minutes of alkaline phosphatase reaction; FIGS. 3b and 3e show the ligation of Pfu polymerase fragment, 15 minutes of alkaline phosphatase reaction; FIGS. 3c and 3f illustrate the TdT reaction, 7 minutes of alkaline phosphatase reaction. FIGS. 3a', 3b', 3c', 3d', 3e', and 3f are the reaction products of the 3 labeling methods using 6-fold longer times of reaction with alkaline phosphatase (90 and 42 minutes respectively).

FIG. 5 shows detection of DNA ends within hydrogen peroxide-treated liver by two labeling methods. The figure shows serial sections using in FIG. 5a the ligation of Taq polymerase fragment, 90 minutes of alkaline phosphatase reaction; and in FIG. 5b the TdT reaction, 42 minutes of alkaline phosphatase reaction.

FIG. 6 shows detection of DNA ends within autolytic bovine adrenocortical tissue. Serial sections were used and the same regions are shown by the three labeling methods. FIG. 6a shows the ligation of Taq polymerase fragment, 15 minutes of alkaline phosphatase reaction; FIG. 6b shows the ligation of Pfu polymerase fragment, 15 minutes of alkaline phosphatase reaction; FIG. 6c shows the TdT reaction, 7 minutes of alkaline phosphatase reaction. FIGS. 6a', 6b', and 6c' are the reaction products of the 3 labeling methods using 6-fold longer times of reaction with alkaline phosphatase (90 and 42 minutes respectively).

FIG. 7 shows detection of DNA ends within heated tissue sections by two labeling methods. Sections of bovine adrenal gland were treated. The figure shows serial sections using, in FIG. 7a, ligation of Taq polymerase fragment, 15 minutes of alkaline phosphatase reaction; FIG. 7b shows the TdT reaction, 7 minutes of alkaline phosphatase reaction.

DETAILED DESCRIPTION OF THE INVENTION DEFINITIONS

Figure 1A:
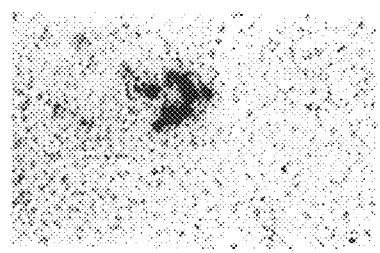
FIG. 1(a) shows ligation of single-base 3' overhang double-stranded DNA fragments prepared by Taq polymerase, using 15 minutes of alkaline phosphatase color development.
Figure 1B:
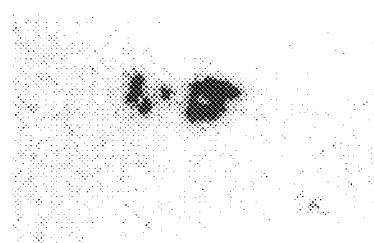
FIG. 1(b) shows ligation of blunt-ended DNA fragment prepared by Pfu polymerase, using 15 minutes of alkaline phosphatase color development.
Figure 1B:
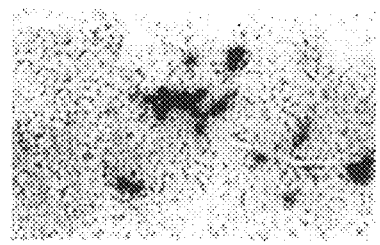
Figure 1C:
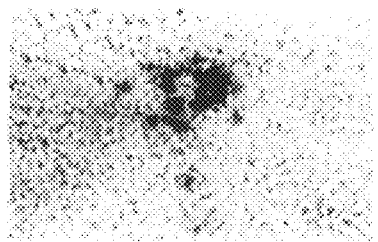
FIG. 1(c) shows extension of 3' hydroxyls with TdT, using 7 minutes of alkaline phosphatase color development.
Figure 1C:
Figure 2A:
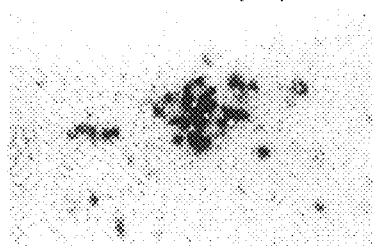
FIGS. 2a and 2c show the reaction products resulting from ligation of Taq polymerase fragment, 15 minutes of alkaline phosphatase reaction.
Figure 2A:
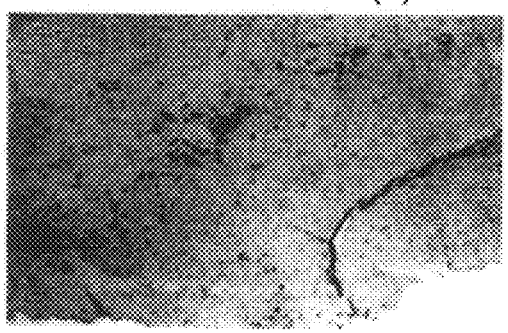
Figure 2C:
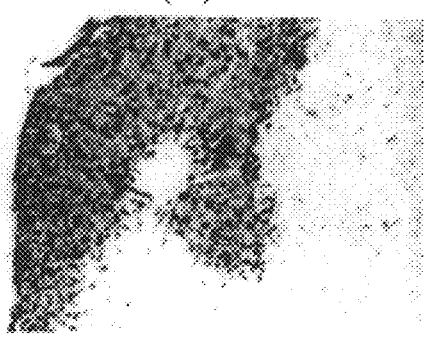
Figure 2B:
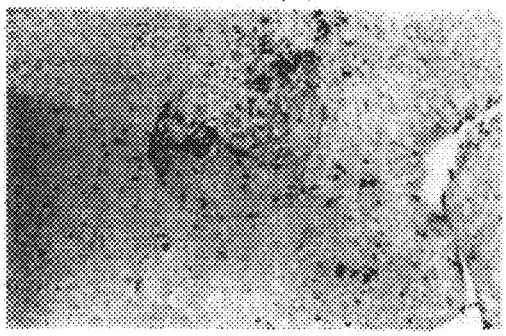
FIGS. 2b and 2d show the TdT reaction, 7 minutes of alkaline phosphatase reaction.
Figure 2D:
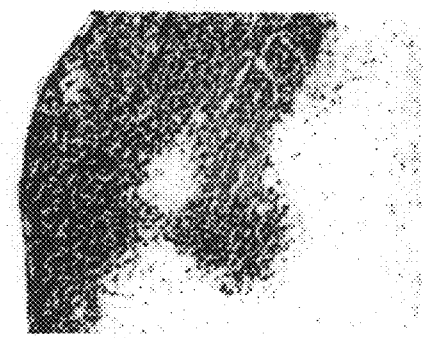

In present application, the term sample shall mean any biological material that contains DNA. The term sample includes, but is not limited to, cells isolated from a multicellular organism, cells grown in cell culture, normal tissue, malignant tissue, necrotic tissue and tissue from any biological source. Biological sources include plant and animal sources.

In the present application, the phrase "DNA having an end characteristic of apoptosis" shall mean any DNA molecule, present in or obtained from a sample, having an end that is ligatable. The DNA of apoptotic cells may be distinguished from that of cells that have undergone necrosis or other forms of cell death in that the ends of the DNA of apotic cells are ligatable. In contrast, the ends of the DNA in cells that have undergone other forms of cell death are not ligatable. The structures of ends produced in the DNA of a cell that has undergone apoptosis include, but are not limited to, ligatable blunt ends, ligatable 3'-overhanging ends and ligatable 5'-overhanging ends. In a preferred embodiment, the DNA having an end characteristic of apoptosis will be a ligatable 3'-overhanging end in which the overhang extends from one to three nucleotides.

In the present application, the phrase "detectable moiety" shall mean any chemical structure or structures the presence or absence of which can be determined. Methods which may be used to determine the presence or absence of the detectable moiety include, but are not limited to, radioactive methods, fluorescent methods and enzyme activity based methods. Those of ordinary skill in the art will appreciate that "detectable moiety" includes, but is not limited to, enzymes, small molecules, chromophores, fluorophores or radio-labeled molecules. Small molecules include, but are not limited to, biotin, digoxigenin, and single atoms such as bromine. In a preferred embodiment, bromine will be used in the form of bromo-deoxyuridine. Radio-labeled molecules include single atoms, such as radioactive iodine, as well as larger molecules.

In the present application, the phrase "reagents for detecting the detectable moiety" shall mean any chemical or chemicals which may be used to determine the presence or absence of a detectable moiety. Examples of "reagents for detecting the detectable moiety" include, but are not limited to, chromogenic substrates for enzymes, fluorogenic substrates for enzymes, enzymes and enzymes conjugated to binding molecules. Binding molecules include, but are not limited to, avidin, streptavidin, lectins, Protein A, Protein G, antibodies and antibody fragments. Also included in reagents for detecting detectable moieties are enzyme cofactors, ATP, buffers, fluors for detecting radioactivity and solid particles such as colloidal gold and polymer coated magnetic particles. Typically solid particles will be conjugated to binding molecules. In a preferred embodiment, "reagents for detection of detectable moieties" will include a binding molecule conjugated to an enzyme. In other preferred embodiments, reagents for detecting detectable moieties will include binding molecules conjugated to fluorescent molecules.

In the present application, the phrase "proteins of apoptotic cells" shall mean any protein or protein fragment expressed by a cell which is undergoing apoptosis. This includes proteins located within the cell as well as those located on the surface of the cell or excreted by the cell.

In the present application, the phrase "RNA of apoptotic cells" shall mean any RNA molecule present in a cell which is undergoing apoptosis. This includes RNA molecules present in the cell prior to the onset of apoptosis as well as those produced during apoptosis.

In the present application a nucleotide probe shall mean any nucleic acid molecule, DNA or RNA, that can be used to detect a different nucleic acid molecule.

In the present application "ligates specifically to the DNA of cells that have undergone apoptosis" shall mean that it is more likely to ligate to DNA of cells that have undergone apoptosis than to ligate to cells that have not undergone apoptosis.

EXAMPLES

The present invention may be more easily understood with reference to the following non-limiting examples.

General Methods

Preparation of Double-strand Nucleic Acid Fragments for in Situ Ligation

In the following specific examples, the present invention is described in terms of DNA probe molecules. Those skilled in the art will readily appreciate that, for the purposes of the present invention, RNA probe molecules are equivalent to DNA probe molecules and could be substituted into the methods and kits of the present invention by simply employing an RNA ligase enzyme instead of a DNA ligase enzyme. Thus, the phrase "nucleic acid," as used herein and particularly in the claims, includes both RNA and DNA molecules.

A 226-bp double-stranded DNA fragment was prepared using primers 5'-GTGGCCTGCCCAAGCTCTACCT-3' (SEQ ID:1) and 5'-GGCTGGTCTGCCGCCGTTTTCGACCCTG-3' (SEQ ID:2) complementary to plasmid pBluescript-bSDI1. Although we used this sequence for the data presented here, the actual sequence of the fragment used is unimportant because we have also used unrelated sequences of lengths 60 to 450 bp with equivalent results. To prepare fragments by the polymerase chain reaction (PCR) with Taq polymerase we set up reactions comprising 100 $\mu$l of 50 mM Tris-HCl, pH 8.3, 10 mM KCl, 1.5 mM $MgCl_2$, 16.6 $\mu$M digoxigenin-11-dUTP (Boehringer Mannheim), 16.6 $\mu$M TTP, 50 $\mu$M dATP, 50 $\mu$M dCTP, 50 $\mu$M dGTP (other nucleotides from Sigma), 100 pmol of each primer, and 10 pg of plasmid. These concentrations of reagents are appropriate for most applications. In some instances, it may be desirable to increase the incorporation of label into the probe and thereby increase the sensitivity of the assay by omitting TTP from the reaction mixture. Taq polymerase (2.5 units, Boehringer Mannheim) was added to each tube when the reaction mixture had been heated to 80° C. PCR was performed with 35 cycles of 20 seconds at 95° C., 20 seconds at 61° C., and 120 seconds at 74° C., the final cycle having an extension time of 4–10 minutes. Fragments were prepared using cloned Pfu polymerase (Stratagene) using the same protocol but with a buffer composition of 200 mM Tris-HCl pH 8.8, 100 mM KCl, 100 mM ammonium sulfate, 20 mM $MgSO_4$, 1% Triton X-100 and 1 mg/ml BSA. Agarose gel electrophoresis of an aliquot of the reaction showed a single product for both enzymes.

To precipitate the fragments, ammonium acetate was added to 2.5 M, the solution was centrifuged at 10,000 g for 5 minutes, and the supernatant was mixed with 2 volumes ethanol and centrifuged for 25 minutes. The supernatant was discarded and the pellet was washed with 70% ethanol and then with 100% ethanol. After vacuum drying for 20 minutes, the pellet was dissolved in water and the concentration measured by Hoechst dye 33258 fluorescence. In an alternative protocol, the PCR reaction mixture was subjected to column purification using silica glass columns (High Pure, Boehringer Mannheim). The fragments were stored at −20° C. until use.

In various embodiments the DNA probe molecule may incorporate different detectable moieties. These detectable moieties may be enzymes, small molecules, chromophores, fluorophores or radio-labeled molecules. Small molecules include, but are not limited to, biotin, digoxigenin, and single atoms such as bromine. In a preferred embodiment, bromine will be used in the form of bromo deoxyuridine. Radio-labeled molecules is seen to include single atoms, such as radioactive iodine, as well as larger molecules.

Preparation of Hairpin Oligonucleotides

We designed oligonucleotide probes capable of detecting double-strand breaks in DNA using a ligation based technique. These oligonucleotides have three portions: 1) a stem formed by complementary sequences in the 3'- and 5'-regions of the oligonucleotide that spontaneously anneal; 2) a loop region in which detectable moieties may be attached; and optionally 3) an overhang portion consisting of one or more unpaired nucleotides located at either the 3'- or 5'-end of the oligonucleotide. These probes specifically and with great sensitivity detect double-strand breaks in apoptotic cells. Localization of these probes is restricted to areas of chromatin characteristic of apoptosis, whereas much more diffuse labeling was obtained when all available 3'-DNA ends were labeled by terminal transferase. Using the principles disclosed herein, hairpin oligonucleotide probes can be designed with any type of 3'- or 5'-overhang complementary to any double-strand DNA termini being detected.

Figure 8:
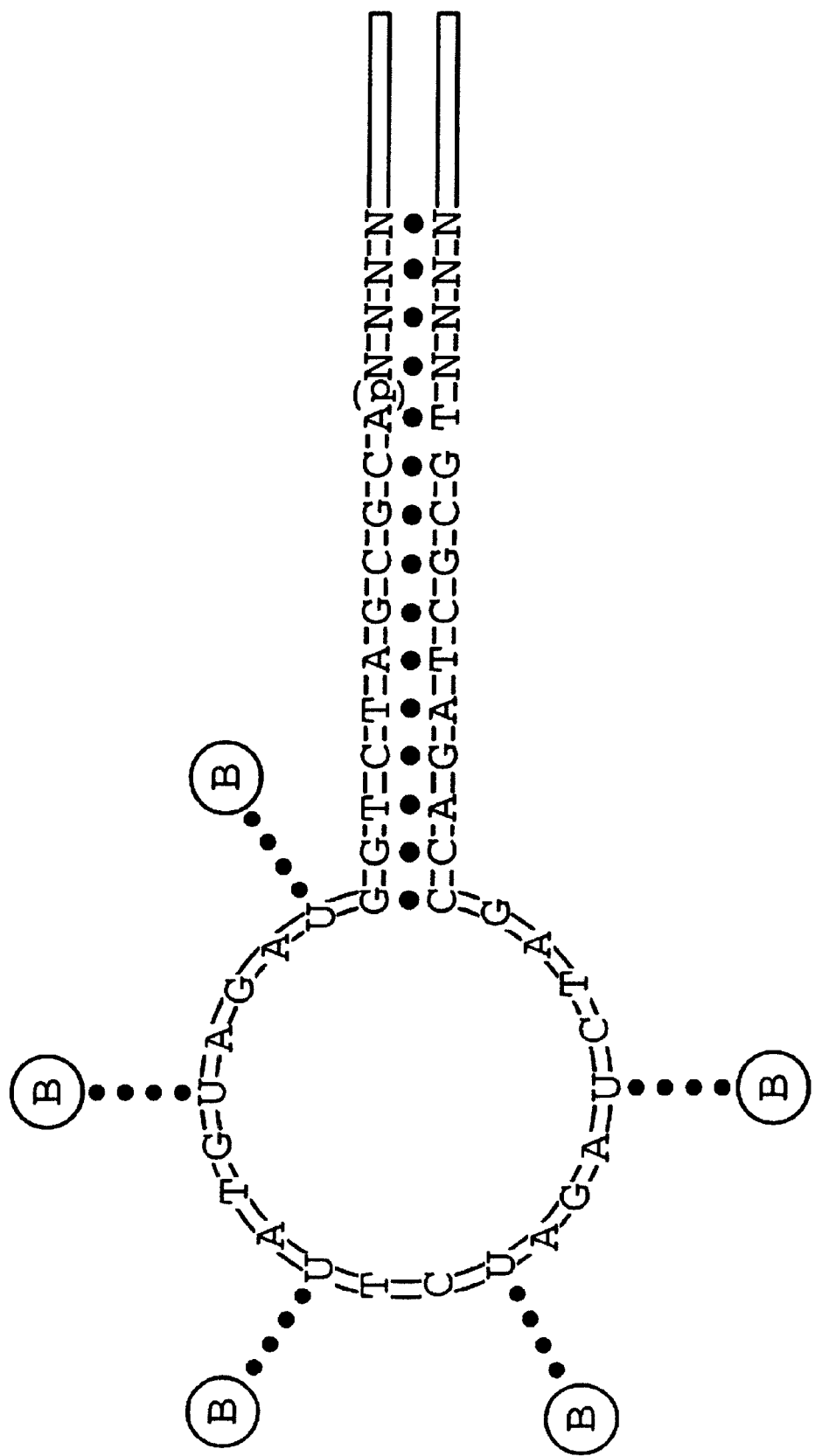
FIG. 8 is a schematic representation of a hairpin oligonucleotide containing an end suitable for ligation.

With the exception of the overhanging portion, the actual sequence of the oligonucleotide is not critical to the functioning of the invention. The critical features of the oligonucleotide are that it spontaneously for a stem structure that can be ligated to compatible DNA ends and that it be detectable when ligated to such DNA ends. One example of a sequence having these characteristics is provided in FIG. 8, SEQ ID:3. This oligonucleotide was designed with a 10-bp stem region to form a hairpin with a defined double-strand end (FIG. 8). The terminus of the stem has a characteristic structure. In the example shown in FIG. 8, the characteristic structure is single 3'-A overhang. The recessed 5'-phosphate of a double-strand break on the tissue section with a single T overhang can ligate to the 3'-A overhang on the probe. The 3'-overhang on the section does not ligate to the recessed 5'-hydroxyl on the probe because the oligonucleotide lacks a 5'-phosphate. This feature avoids the possibility of the probe ligating to 3'-hydroxyls on the ends of single-stranded DNA fragments.

A loop of 20 nucleotides was designed to accommodate detectable labels without base-pairing in this region. The size of the loop may be varied from as few as one base to as many bases as desired. Alternatively, the loop may be entirely dispensed with and replaced by one or more non-nucleotide moieties. These non-nucleotide moieties may include sugar residues without bases or other chemical structures that allow the incorporation of a detectable label.

The loop exemplified in FIG. 8 contains 5 deoxyuridine derivatives labelled with biotin (B). At 5 places in the loop, the oligonucleotide was synthesized with amino modifier C6-deoxyuridine (Glen Research, Sterling, Va.). After synthesis of the oligonucleotide, the detectable moiety biotin was covalently attached to the amino groups by reaction with biotin bis-aminohexanoyl N-hydroxysuccinimide ester (Glen Research). The synthesis and post-synthesis biotinylation were performed by Synthetic Genetics Corp. (San Diego, Calif.). Alternatively, the hairpin was synthesized with the substitution of a preformed biotin-labeled thymidine analogue (Glen Research). In addition, any other means of incorporating a detectable label into the hairpin oligonucleotide that does not interfere with the ability of the nucleotide to be ligated may be used. This includes and is not limited covalent attachment using nucleotides other than C6-deoxyuridine as well as incorporation of non-nucleotide moieties into the oligonucleotide. As long as the stem and any overhang structure are not disrupted, any form of incorporation of a detectable label may be used.

In the specific example presented here, biotin was used as a detectable label. Those skilled in the art will readily appreciate that other conventionally used detectable labels may be used in place of biotin. Placing the detectable moiety in the loop away from the stem of the hairpin avoids potential interference of a large detectable moiety with the enzymatic linkage of the probe to the section by ligase, thus permitting the use of a great variety of detectable moieties including large detectable moieties such as enzymes and other proteins.

Although the present example shows the use of 5 detectable labels in each oligonucleotide, those skilled in the art will appreciate that the number of labels incorporated in each oligonucleotide can be varied. Increasing the number will result in a greater signal being seen for each DNA end present. This may be desirable in samples containing a relatively small number of DNA ends capable of ligation. Conversely, reducing the number of detectable labels present in each oligonucleotide will reduce the signal generated by each ligated DNA end. Those skilled in the art will recognize the desirability of empirically determining the optimum number of labels to incorporate in each oligonucleotide in order to optimize the signal/background ratio for any given application and tissue source.

Probes with three different types of ends were used in these experiments: blunt-ended, single 3'-A overhang, and random sequence, two nucleotide 3'-overhang (3'-NN). Clearly, by modifying the sequence of the oligonucleotide, longer overhangs, either 3'- or 5'-overhangs, may be created. For some applications, such as detection of cleavage of DNA by nucleases that produce a defined end, it may be desirable to synthesize the oligonucleotide such that an overhang of defined length and sequence is produced. In other instances, such as the 3'-NN oligonucleotide tested, the oligonucleotide may be formed with an overhang of defined length wherein the sequence of the overhang has been randomized. This will result in a mixture containing (4)n different sequences of oligonucleotides where n=the number of nucleotides in the overhang.

In the two base overhang case exemplified, the oligonucleotide mixture contained 16 different sequences of nucleotide. As the mixture contained oligonucleotides having all possible bases in all possible positions of the overhang, the mixture detected any two base 3'-overhang. Synthesis of such mixtures of oligonucleotides can easily be accomplished during synthesis by using a reagent mixture containing all nucleotides at positions where randomization is desired. Alternatively, each individual sequence may be synthesized separately and then the separate sequences mixed. The latter technique may be used to form mixtures that contain oligonucleotides having less than all possible bases at all positions in order to detect a subset of all cleavages. In other embodiments of the invention, it may be desirable to randomize some positions in the overhang while holding some other positions of the overhang constant.

For certain applications, it may be desirable to package the oligonucleotide probes and required reagents as kits. The kits may contain oligonucleotides having a variety of ends. For example, the kit may contain blunt ended oligonucleotides in addition to one, two and three base overhang oligonucleotides where the overhangs could be either 3'or 5'or both. The oligonucleotides may be provided as individual separate oligonucleotides or as mixtures of oligonucleotides. The mixtures may be of all oligonucleotides containing a given length and type overhang (i.e., 3'or 5'). Alternatively, the mixtures may contain only some of the possible oligonucleotides of a given length and type overhang. In other embodiments, it may be desirable to provide the oligonucleotides as mixtures containing more than one length and/or type overhang. For example, a may might contain all two base overhangs of both the 3' and 5' type; or, a may might contain one, two and three base overhangs of a specific type, 3' or 5'. The contents of a mixture of oligonucleotides can be varied depending on the type of DNA end believed to be present in the DNA of interest.

Kits of the present invention may also include reagents useful in conducting the methods of analysis of DNA ends set forth herein. These reagents may include DNA ligase enzymes, buffers and other enzymes including proteases and signal generating enzymes such as glucuronidases, luciferases and the like. Other reagents which may be included in the kits of the present invention include substrates for signal generating enzymes, antibodies that recognize detectable moieties and other reagents that permit the identification of the detectable moieties.

Ligation of Labeled DNA Fragments

Digoxigenin-labeled probe fragments were ligated to DNA in tissue sections in situ using T4 DNA ligase. Various tissues (described in Examples) were used with the following protocol. Tissue fragments were fixed in either freshly prepared paraformaldehyde or buffered formaldehyde, with equivalent results, and were conventionally dehydrated and embedded in paraffin. 6-$\mu$m sections were treated with xylene to remove the paraffin and rehydrated in graded alcohol concentrations. The rehydration was accomplished by incubating the sample in xylene for 5 minutes then replacing the xylene with fresh xylene and incubating a second 5 minute interval. The xylene was removed and the sample was incubated in 100% ethanol for 5 minutes. The ethanol was then removed and fresh 100% ethanol was added. The sample was incubated for an additional 5 minutes in 100% ethanol. The ethanol was then replaced with 96% ethanol and the sample was incubated for 30 seconds. The 96% ethanol was then replaced with 80% ethanol and the sample was incubated for 30 seconds. The 80% ethanol was then removed and the sample washed in water.

Ligations involving digoxigenein-labelled, double-stranded DNA fragments were performed according to the following protocol. All the following procedures were performed at room temperature (23° C.). The de-paraffinized sections were incubated with 50 $\mu$g/ml proteinase K in PBS for 30 minutes, then rinsed thoroughly with water. A mix of 50 mM Tris-HCl, pH 7.8, 10 mM $MgCl_2$, 10 mM DTT, 1 mM ATP, 25 $\mu$g/ml BSA, 15% polyethylene glycol (8000 m.w., Sigma), with the digoxigenin-labeled DNA fragment at 1 $\mu$g/ml and DNA T4 ligase (Boehringer Mannheim) at 25–100 units/ml was added (20 $\mu$l per section). Sections were covered with glass coverslips and placed in a humidified box for 1–16 hours. The sections were thoroughly washed in water and then pre-blocked with blocking solution (Boehringer Mannheim), reconstituted as recommended by the manufacturer, for 15 minutes. Additional washes with 70° C. water can be used to inactivate endogenous alkaline phosphatases if excessive background staining is observed. The blocking solution was removed and sheep anti-digoxigenin Fab fragment-alkaline phosphatase conjugate (Boehringer Mannheim), 1:100 dilution in blocking buffer, was added for 10 minutes, followed by washing in 0.1 M Tris-HCl, pH 7.5, 0.1 M NaCl, 2 times for 10 minutes each. For color development, sections were then placed in the solution recommended by the manufacturer (0.1 M Tris, pH 9.5; 0.1 M NaCl; 167 $\mu$g/ml 5-bromo-4-chloro-3-indolyl phosphate; 330 $\mu$g/ml nitro blue tetrazolium) and the color development was monitored under the microscope. The reaction was stopped by washing sections in water. The wet sections were photographed without counterstain.

Ligations involving hairpin oligonucleotides were conducted according to the following protocol at room temperature (23° C.). Sections were incubated with 25 $\mu$g/ml proteinase K (Oncor, Gaithersburg, Md.) in PBS for 5 minutes. Those of ordinary skill in the art will recognize that the time of incubation may be decreased or increased for optimization of signal and background in different tissues. Sections were then rinsed thoroughly with water. A mix of 50 mM Tris-HCl, pH 7.8, 10 mM $MgCl_2$, 10 mM DTT, 1 mM ATP, 15% polyethylene glycol (8000 m.w., Sigma), with hairpin oligonucleotides at 35 $\mu$g/ml and DNA T4 ligase (Boehringer Mannheim, Indianapolis, Ind.) at 250 units/ml was added (20 $\mu$l per section). Sections were covered with glass coverslips and placed in a humidified box for 16 hours. The sections were then washed with several changes of water over 2 hours. Fluorescein-avidin conjugate (Vector Laboratories, Burlingame, Calif.) was added at 4 $\mu$g/ml in 50 mM sodium bicarbonate, 15 mM sodium chloride, pH 8.2, for 45 minutes. Sections were washed in the same buffer 3 times over 30 minutes and then in water for 20 minutes.

The ligation reaction may also be performed on isolated DNA that has been size fractionated on an agarose gel. The DNA is first transferred to a solid support by any conventional means, i.e. capillary action, vacuum blotting or electroblotting. The solid support is then blocked and the ligation reaction conducted as above.

Terminal Deoxynucleotidyl Transferase (TdT) Reaction

In order to provide a comparison to the prior art method of identifying apoptotic cells, parallel tissue samples were analyzed using the TdT reaction. For the reaction of available DNA 3'-hydroxyls with TdT, the published procedure was used modified to accommodate the use of digoxigenin or Texas Red as label rather than biotin. When digoxigenin was used as label, instead of addition of ligase mixture as above, a mixture comprising 30 mM Tris-HCl, pH 7.2, 140 mM sodium cacodylate, 1 mM cobalt chloride, 0.1 mM DTT, 50 $\mu$m digoxigenin-dUTP and 300 units/ml TdT (Promega) (20 $\mu$l per section) was added for 1 hour at 37° C. in a humidified incubator. The washing and visualization of incorporated digoxigenin was as described above.

When Texas Red was used as a label, a mixture comprising 30 mM Tris-HCl, pH 7.2, 140 mM sodium cacodylate, 0.1 mM DTT, 8 $\mu$M Texas Red-X dUTP (Molecular Probes, Eugene, Oreg.) and 800 units/ml terminal transferase (Boehringer-Mannheim) (20 $\mu$l per section) was added for 1 hour at 37° C. in a humidified incubator. Following washing in water (2 changes over 20 minutes) the sections were counterstained with the DNA-binding dye 4,6-diamidino-2-phenylindole (DAPI) (1 $\mu$g/ml), mounted in Vectashield (Vector Laboratories) and observed by fluorescence microscopy.

Tissues

Thymus: To prepare tissue that contained a large number of apoptotic cells, Sprague-Dawley rats (150 g) were injected subcutaneously with 6 mg/kg dexamethasone (Sigma) dissolved in 30% dimethyl sulfoxide in water. Animals were killed after 24 hours and the thymus was fixed in 4% paraformaldehyde. Thymus from control animals was obtained and fixed in the same way. After 18 hours in paraformaldehyde the tissue fragments were placed in 70% ethanol and taken through graded alcohols to 100% ethanol, placed overnight in chloroform, and then embedded in paraffin.

Necrotic tissue: Sections from a Wilms' tumor from a 5-year old male patient, containing extensive areas of necrosis, as often encountered in such tumors, was used as to provide sections with large numbers of necrotic cells.

Hydrogen peroxide treated liver: Random DNA damage was induced by injection of hydrogen peroxide. Sprague-Dawley rats were anesthetized and 100 µl of 30% hydrogen peroxide was injected superficially in the liver in several locations. After 20 seconds the liver was excised from the animal and the hydrogen-peroxide-treated segment of the liver was fixed in 4% paraformaldehyde, with multiple changes of the solution to remove any remaining hydrogen peroxide. Segments of tissue from a distal region of the liver were fixed as controls. The tissues were then processed as described for thymus.

Kidney: Mild trauma of the kidney was achieved by puncturing the capsule and loosening it away from the parenchyma. This resulted in a zone of apoptotic cells close to the site of trauma 24 hours later. Mild injury to the kidney results in apoptosis of epithelial cells associated with tubular degeneration.

Tissue for in vitro autolysis: 5-mm fragments of bovine adrenal gland were placed in culture medium in a 37° C. incubator for 16 hours. They were then fixed and processed as described for thymus.

Heated tissue sections: Sections from a control bovine adrenal gland were de-paraffinized, rehydrated through graded alcohol concentrations, placed in 0.01 M sodium citrate, pH 6.0, and heated at 100° C. for 5 minutes.

Spotting of Digoxigenin-labeled DNA on Nylon

Different amounts of digoxigenin-labeled DNA (synthesized by random-primer method, Boehringer Mannheim) were spotted on Hybond-N membranes (Amersham) as previously described. The digoxigenin fixed to the membranes was detected using the same protocol as described above for tissue sections, except that anti-digoxigenin-alkaline phosphatase conjugate was used at 1:5000 dilution.

Preparation of Probe Fragments with Varying Overhangs

PCR is performed on a DNA template that includes a DNA sequence that functions as the recognition site for a restriction enzyme. The PCR product is purified and isolated by standard means. The PCR is performed in the presence of a small amount of dideoxynucleotides. This results in fragments that terminate in a dideoxynucleotide. These fragments do not contain a 3'-hydroxyl group and cannot be ligated into target DNA.

The PCR product is then digested with a restriction enzyme that recognizes the included site. Cleavage with a restriction endonuclease generates 3'-OH at the cleavage site. Fragments thus cleaved can be ligated into target DNA. The characteristics of the termini of the digested fragment will be determined by the restriction enzyme chosen. By incorporating two identical appropriately spaced recognition sites into the DNA template, fragments having defined termini can be produced. Alternatively, two oligonucleotides having complementary regions and overhanging regions can be synthesized. The oligonucleotides can be annealed by standard techniques. Information concerning restriction enzyme recognition sites, appropriate digestion conditions and the characteristics of the resulting termini are readily available to one skilled in the art by consulting a standard text such as Sambrook et al., Molecular Cloning: A Laboratory Manual 2nd Edition, Cold Spring Harbor Press, specifically incorporated herein by reference.

Analyzing DNA to Determine the Types of Termini Present

The termini produced by various nuclease enzymes have previously been determined. By determining the types of termini present in a DNA sample, it is possible to gain information about the nuclease enzymes that have acted upon the DNA. To determine if the DNA in a given sample has been acted upon by a nuclease, the DNA is probed with various nucleic acid fragments. Each nucleic acid fragment used as a probe will have termini capable of ligating to the termini produced by a specific type of nuclease. By determining which fragment can be ligated to the DNA sample, it is possible to determine what nuclease has acted upon the sample. This process may be conducted by dividing the sample into aliquots and probing each aliquot with a different fragment. Alternatively, multiple fragments may be tested simultaneously on the same sample. In this case, the fragments may be distinguished from each other by the incorporation of different detectable moieties. The detectable moieties may be enzymes, small molecules, chromophores, fluorophores, or radio-labeled materials. Those skilled in the art can readily select suitable detectable moieties so as to permit the simultaneous detection of each moiety.

In a preferred embodiment, a number of double stranded nucleic acid probe molecules, either DNA or RNA or a mixture of both, can be fixed to different regions of a solid support. A DNA sample suspected of containing termini generated by the action of one or more nucleases, may be brought into contact with the fixed nucleic acid probe molecules in the presence of appropriate ligase enzymes and co-factors (metal ions, ATP, buffers, etc.).

The DNA sample is incubated with the nucleic acid probe molecule at an appropriate temperature of from about 10° C. to about 37° C. for an appropriate length of time of about 30 minutes to about 16 hours. After incubation, the solid support may be washed to remove any unligated DNA and the presence of DNA ligated to the probe molecules is detected.

In an alternative embodiment, an aliquot of the DNA suspected of containing termini created by the action of one or more nuclease enzymes may be fixed to a solid support using any art recognized means, such as, for example, UV treatment. The fixed DNA can then be contacted with a solution containing one or more nucleic acid probe molecules, DNA, RNA, or a mixture of both, and the appropriate ligase enzymes. The probe molecules will be selected to contain detectable moieties. The detectable moieties will be selected so that each moiety will be detectable in the presence of the detectable moieties present on the other nucleic acid probe molecules and, ideally, all moieties will be simultaneously detectable.

After a suitable period of time to permit the ligation of the probe molecules to the DNA termini present in the aliquot, the solid support may be washed and the presence of nucleic acid probe molecules detected.

The detection of nucleic acid probe molecules will be performed using art recognized methods. For example, the nucleic acid probe molecule may incorporate a detectable moiety that can be directly detected. In this embodiment, the detectable moiety may be a chromophore, fluorophore, or enzyme.

In an alternative embodiment, the nucleic acid probe molecules will include detectable moieties that can be bound by a reagent comprising a molecule having a binding portion and a signaling portion. Examples of suitable binding portions include, but are not limited to, avidin, streptavidin, antibodies, and antibody fragments. Preferred embodiments include a detectable moiety that is a bromine atom incorporated into a nucleic acid probe molecule and a binding portion that comprises an anti-bromine antibody. Other preferred embodiments include detectable moieties that are biotin or biotin analogs and binding portions that comprise avidin or streptavidin. Other preferred embodiments utilize digoxigenin as a detectable moiety and a binding portion that comprises an anti-digoxigenin antibody or antibody fragment.

In embodiments that utilize a reagent that comprises a molecule that binds to a detectable moiety, the molecule may also comprise a signaling portion that permits detection of the presence of the reagent. For example, the reagent may comprise a molecule having a binding portion that binds to the detectable moiety, and the molecule may additionally comprise a signaling portion that permits detection of the molecule. Examples of signaling portions include enzymes, chromophores, fluorophores, and radio labeled material. Thus, the molecule may comprise a binding portion covalently attached to a signaling portion. Examples include, but are not limited to, avidin or streptavidin covalently attached to enzymes, such as luciferases, peroxidases, galactosidases, glucuronidases, and phosphatases. Preferred embodiments will use streptavidin covalently attached to horseradish peroxidase. Other preferred examples include antibodies coupled directly with enzymes. Those skilled in the art are aware that such coupling may be accomplished using a variety of coupling reagents such as those sold by Pierce Chemical Co. of Rockford, Ill. Examples include anti-bromine antibody coupled to enzymes. Preferred examples include anti-bromine antibody attached to horseradish peroxidase.

In some embodiments of the instant invention, detection of the detectable moiety is accomplished by contacting the detectable moiety with a reagent that comprises a first molecule that binds to the detectable moiety and then subsequently applying a reagent that comprises a second molecule that binds to the first molecule. For example, when the detectable molecule is bromine, the sample may be contacted with a reagent that comprises an anti-bromine antibody or antibody fragment. The sample may then be contacted with a reagent that comprises a second molecule that binds to the anti-bromine antibody or antibody fragment. Examples include, but are not limited to, reagents comprising protein A, lectins, and antibodies that bind to the anti-bromine antibody coupled to a signaling portion. The second molecule may contain a signaling portion. The signaling portion may include an enzyme, chromophore, fluorophore, or radio-labeled material. The preparation and utilization of such second molecules are well known to those skilled in the art. (See, for example, chapter 18 of Sambrook, et al.) Other examples include the use of biotin or biotin analogs as detectable moieties, streptavidin or avidin as first molecules, and anti-streptavidin or anti-avidin antibody or antibody fragments coupled to signaling portions as second molecules. Other preferred embodiments utilize digoxigenin as detectable moieties, anti-digoxigenin antibodies as first molecules, and antibodies directed against the anti-digoxigenin antibodies coupled to signaling portions as second molecules.

In embodiments that utilize a first binding molecule to bind a detectable moiety and a second molecule to bind the first molecule, the second molecule may contain a signaling portion. The signaling portion may be any signaling portion known in the art. Signaling portions of the present invention include, but are not limited to, chromophore, fluorophores, enzymes, and radio-labeled material. When the signaling portion is a chromophore or fluorophore, the presence of the signaling portion may be detected visually or with the use of devices that measure optical density. When utilizing optical density readers, it may be desirable to place the sample on or in a solid support that is transparent at the wavelength at which the chromophore absorbs or at the wavelengths at which excitation and emission of the fluorophore occur. This methodology may be useful to quantify the presence of termini generated by specific nucleases. Transparent solid supports are seen to include, but are not limited to, transparent test strips and microtiter plates.

When the signaling portion is an enzyme, the method will include a step of providing the enzyme with a substrate. The substrate may be provided as part of the reagent comprising the second molecule. Alternatively, the substrate may be provided after the reagent comprising the second molecule. When the enzyme reacts with the substrate, some measurable change must take place. For example, the enzyme may convert a colorless substrate molecule into a colored product molecule. Alternatively, a colored substrate molecule may be converted into a colorless product molecule. In some instances, one of the products of the enzyme reaction may be a photon of light. In these instances, the quantity of photons of light produced can be measured. The available enzymes and appropriate substrates and quantitative methodologies are well known to those skilled in the art.

Example 1

Detection of High Concentrations of Double-stranded DNA with Single-base 3'-overhangs, as well as Blunt-ended DNA and Free 3'-hydroxyls, in Apoptotic Cells Rat thymus was fixed and processed by three labeling methods as described in the General Methods. FIG. 1 shows the reaction products resulting from (a) ligation of single-base 3' overhang double-stranded DNA fragment prepared by Taq polymerase, using 15 minutes of alkaline phosphatase color development; (b) ligation of blunt-ended DNA fragment prepared by Pfu polymerase, using 15 minutes of alkaline phosphatase color development; (c) extension of 3' hydroxyls with TdT, using 7 minutes of alkaline phosphatase color development. a', b', and c' are the reaction products of the 3 labeling methods using 6-fold longer times of alkaline phosphatase color development (90 and 42 minutes respectively).

To obtain a tissue with many apoptotic cells we initially used rat thymus 24 hours after administration of glucocorticoid, a model for apoptosis well established by previous investigators. However, control rat thymus also had a lower but useful number of apoptotic cells, consistent with the observation that about 1% of thymic cells show features of cell death in postnatal animals. Because control thymus tissue sections were not affected by the severe atrophy found in glucocorticoid-treated thymus, we used the apoptotic cells in control thymus as our standard for the investigation of DNA ends, but we show also for comparison the results in thymus from dexamethasone-treated animals.

Consecutive 6 $\mu$m sections were labeled with single-base 3' overhang and blunt-ended DNA fragments, using the same concentration of fragment and the same period of time of incubation with ligase. Consecutive sections were also labeled with TdT. In all cases the digoxigenin fixed to the section by the action of ligase or TdT was detected using an anti-digoxigenin-alkaline phosphatase conjugate. We assessed the length of time of the color development in the alkaline phosphatase reaction which just allowed the visualization of apoptotic cells. A reaction time of 7 minutes in the case of TdT and 15 minutes for ligase (using either 3'-overhang or blunt-ended DNA fragments) was sufficient to label apoptotic cells in thymus sections. When 6-fold longer times of color development were used, the same number of nuclei were labeled, using all three techniques, with very little background staining.

Example 2

Comparison of Patterns of Apoptotic Cells, Detected by the Presence of Different Types of DNA Ends, in Control and Glucocorticoid-treated Thymus We compared the labeling of cells by ligation of 3'-overhang fragments to the labeling of cells by reaction of accessible 3'-hydroxyls with TdT, in both control and glucocorticoid-treated thymus (FIG. 2). The numbers and patterns of cells stained by both methods in thymic cortex in control and glucocorticoid-treated animals were consistent with the previously reported numbers and patterns of apoptotic cells in control animals and in animals 24 hours after glucocorticoid administration.

Thymus from control (a, b) and glucocorticoid-treated (c, d) rats were fixed and processed as described in Example 1. FIG. 2 shows the reaction products resulting from (a, c) ligation of Taq polymerase fragment, 15 minutes of alkaline phosphatase reaction; (b, d) TdT reaction, 7 minutes of alkaline phosphatase reaction.

Example 3

Detection of DNA Ends within Necrotic Cells in Wilms' Tumor by Three Labeling Methods To compare the occurrence of single-base 3' overhangs, blunt ends, and all accessible 3'-hydroxyls in apoptotic and necrotic cells, we performed simultaneous staining of both apoptotic and necrotic tissue. The methods used were as described in Example 1.

Sections of Wilms' tumor, containing large areas of necrosis, were used as a standard for a tissue comprising many necrotic cells. Consecutive sections were used to enable comparison of the reaction of different methods on various areas within this heterogeneous tissue. Staining reactions were performed for two different times, as used in the detection of apoptotic cells in thymus: a time sufficient for visualization of apoptotic cells (7 or 15 minutes) and a time 6-fold longer. To ensure that these times were appropriate, sections of rat thymus were mounted on the slide together with the necrotic tissue and processed in the same labeling solutions.

Serial sections were used and the same regions are shown by the three labeling methods and presented in FIG. 3. FIGS. 3a and 3d show ligation of 3'-overhang Taq polymerase fragment, 15 minutes of alkaline phosphatase reaction; FIGS. 3b and 3e show ligation of the blunt Pfu polymerase fragment, 15 minutes of alkaline phosphatase reaction; FIGS. 3c and 3f show TdT reaction, 7 minutes of alkaline phosphatase reaction. a', b', c', d', e', and f' are the reaction products of the 3 labeling methods using 6-fold longer times of reaction with alkaline phosphatase (90 and 42 minutes respectively).

In necrotic areas of the specimen, the TdT reaction produced intense labeling even with 7 minutes of alkaline phosphatase color development (FIG. 3c and 3f). In purely necrotic regions (FIG. 3, a–c), ligation of both 3'-overhang and blunt-ended fragments produced very little staining even with 6-fold longer color development than required for visualization of apoptotic cells. In adjacent areas of the tumor, where some tissue structure was preserved (FIG. 3, d–f), extensive staining of nuclei with TdT was again observed. Distinct labeling of nuclei was also observed with 6-fold overdevelopment of the color reaction in the case of blunt-ended fragment, but hardly at all with the 3'-overhang fragment.

The fact that the 3'-overhang fragment did not produce a signal in the necrotic areas (FIG. 3a) and generated a strong signal in the apoptotic areas (FIG. 3d) leads to the conclusion that single-base 3' overhangs are specific for apoptotic cells.

Example 4

Relative Color Development of Spots with Various Amounts of Digoxigenin-labeled DNA The indicated amounts of digoxigenin-labeled DNA were spotted onto nylon membranes as described in Methods and then processed for detection of digoxigenin by the alkaline phosphatase reaction. The extent of color development at 15 and 90 minutes is shown.

Figure 4:
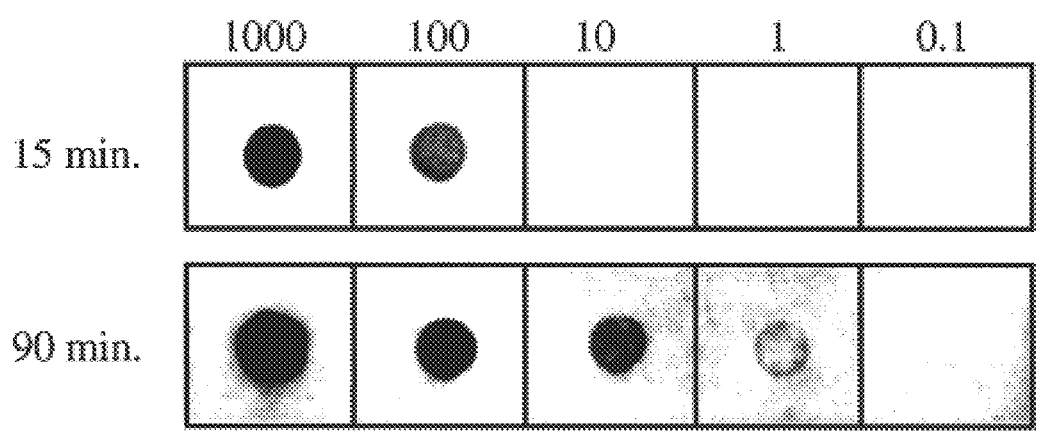
FIG. 4 shows relative color development of spots with various amounts of digoxigenin-labeled DNA.

To provide an estimate of the relative abundance of single-base 3'-overhangs in apoptotic versus necrotic tissue, a series of spots of digoxigenin-labeled DNA on nylon was stained by alkaline phosphatase color development using the same two times used for tissue sections (FIG. 4). This experiment shows that 90 minutes versus 15 minutes of color development allows the visualization of almost 100-fold less digoxigenin. Since apoptotic nuclei in thymus are readily detectable by ligation of 3'-overhang fragment using 15 minutes of color development, but nuclei in necrotic tissue are hardly stained with 90 minutes of color development, it may be concluded that apoptotic nuclei have at least 100-fold more single-base 3' overhangs than necrotic nuclei.

Example 5

Testing of the 3'-overhangs in Cells with DNA Damage

In order to assess the specificity of the present methodology, we tested whether DNA ends that can be ligated to 3'-overhang DNA fragment were present in cells with other types of DNA damage that might be produced in vivo (e.g., oxygen free radical DNA strand breakage), or by postmortem autolysis, or by in vitro procedures that damage DNA (e.g. heating, as used in antigen retrieval procedures). In order to assess this, detection of DNA ends within hydrogen peroxide-treated liver by two labeling methods.

The methods used were as described in Example 1. FIG. 5 shows serial sections using (a) ligation of Taq polymerase fragment, 90 minutes of alkaline phosphatase reaction; (b) TdT reaction, 42 minutes of alkaline phosphatase reaction.

To provide rapid damage by oxygen radicals, at such a short time that apoptotic cell death was unlikely, hydrogen peroxide was injected into the liver of an anesthetized rat, and segments of liver were fixed 20 seconds later. This tissue showed many areas of nuclei with 3' ends accessible to TdT but no 3' overhangs (FIG. 5).

Example 6

Detection of DNA Ends within Autolytic Bovine Adrenocortical Tissue

The methods used were as described in General Methods. Serial sections were used and the same regions are shown by the three labeling methods. FIG. 6 shows (a) ligation of Taq polymerase fragment, 15 minutes of alkaline phosphatase reaction; (b) ligation of Pfu polymerase fragment, 15 minutes of alkaline phosphatase reaction; (c) TdT reaction, 7 minutes of alkaline phosphatase reaction. a', b', and c' are the reaction products of the 3 labeling methods using 6-fold longer times of reaction with alkaline phosphatase (90 and 42 minutes respectively).

Autolysis was produced within the centers of fragments of bovine adrenal cortex incubated in medium at 37° C. for 16 hours. Again using times of alkaline phosphatase color development suitable for the detection of apoptotic cells within rat thymus, no cells were stained by ligation of 3'-overhang fragments, cells were lightly stained with blunt-end fragment ligation, and markedly stained by TdT extension of 3' ends (FIG. 6, *a–c*). With 6-fold overdevelopment of the color reaction, light staining was apparent in the sections with 3'-overhang ligation whereas staining with blunt-end fragment and TdT became more intense (FIG. 6, *d–f*).

Example 7

Detection of DNA Ends within Heated Tissue Sections by Two Labeling Methods Sections of bovine adrenal gland were treated as described in Methods. FIG. 7 shows serial sections using (a) ligation of Taq polymerase fragment, 15 minutes of alkaline phosphatase reaction; (b) TdT reaction, 7 minutes of alkaline phosphatase reaction.

To test the effects of heat, 6-$\mu$m sections of control bovine adrenal gland were heated at 100° C. for 5 minutes followed by ligation of 3'-overhang fragment or detection of accessible 3' ends (FIG. 7). Some nonspecific staining was noted in sections with ligation of 3'-overhang fragment but nuclei were not stained. In contrast, TdT labeling of nuclei was extensive in heated sections.

Example 8

Detection of the Presence of Apoptotic Cells in a Tissue Sample

DNA present in a sample is isolated according to standard methodologies (see Sambrook, et al.). The DNA is size fractionated on agarose and then transferred to a solid support. The solid support is generally in the form of a membrane. The membrane may be constructed of any commonly utilized materials, such as nylon, PVDF or nitrocellulose. The transfer may be accomplished by any commonly utilized methodologies. These methodologies are considered to include capillary action, vacuum blotting and electroblotting.

After the DNA has been transferred to the solid support, the solid support is blocked using known blocking solutions. Subsequent to blocking, the solid support is contacted with the solution containing a DNA probe molecule specific for a target DNA, a DNA ligase enzyme, and the requisite co-factors. The ligation reaction may be conducted at a temperature from about 4° C. to about 37° C. Preferably, the ligation reaction may be conducted at a temperature from about 10° C. to about 37° C. and most preferably at a temperature from about 15° C. to 37° C. One skilled in the art will readily recognize that it is necessary to prevent the solid support from drying out during the process of the ligation reaction. In order to accomplish this, the ligation reaction may be conducted in a sealed container, such as, for example, a sealed plastic bag or a roller bottle or any commonly used device known to those skilled in the art. After completion of the ligation reaction, the solid support is washed and the DNA probe molecule is detected as described above.

Example 9

Simultaneous Detection of 3' Overhangs and Proteins in the Same Apoptotic Cell The instant invention permits the simultaneous detection of:

1) DNA molecules characteristic of apoptotic cells; and
2) the protein molecules that are expressed in the same apoptotic cell.

This will allow the characterization of the protein expression of cells undergoing apoptosis. Tissue samples are fixed and embedded in paraffin as described above. The samples are then de-paraffinized and rehydrated through graded alcohol concentrations as described above. The proteinase K step described in the basic protocol is omitted. Instead, the sample is placed in buffer and heated. The samples may be heated by placing them in a sealed container and placing the sealed container in boiling water or, alternatively, may be heated by placing them in buffer and heating the buffer solution in a microwave oven. The samples are heated to a temperature greater than 70° C. and maintained at that temperature for at least 15 minutes. The buffer used may be any commonly available buffer. In a preferred embodiment, the buffer is 0.01 M citrate at a pH of 6.0.

After heating, the samples are cooled and contacted with a solutions containing a DNA probe, a DNA ligase enzyme, the co-factors necessary for the ligase reaction to proceed, and an antibody specific to a protein of interest. The antibody is detected using standard methods and the DNA probe molecule is detected as described above. The presence of the antibody and the DNA molecule in the same cell indicates that the protein for which the antibody is specific is present in apoptotic cells.

In a preferred embodiment, after heating, a first antibody may be applied to the sample and incubated for an appropriate period of time, such as from about 5 minutes to about 48 hours, at an appropriate temperature, such as from about 4° C. to about 37° C. The selection of appropriate times and temperatures is dependent upon the characteristics of the antibody-protein interaction and is well within the skill of the ordinary practitioner in the art.

The sample is then washed with 0.1 M Tris-NaCl at a pH of 7.5 two times for 10 minutes each. The sample is then contacted with a solution containing a secondary antibody conjugated to a detectable moiety. In various embodiments, the detectable moiety may be an enzyme, a small molecule, a fluorophore, a chromophore or a radio-labeled molecule. In a preferred embodiment, the enzyme will be an alkaline phosphatase.

The sample is incubated with the secondary antibody for an appropriate period of time, such as from about 5 minutes to about 24 hours, at an appropriate temperature such as from 4° C. to 37° C. In a preferred embodiment, the secondary antibody is incubated with the sample at room temperature for 30 minutes. The sample is then washed in a buffer solution, such as Tris-NaCl at pH 7.5. When the detectable moiety is an enzyme, the sample is contacted with a solution containing a detection reagent. The detection reagent may commonly be a molecule that serves as a substrate for the enzyme conjugated to the secondary antibody. The reaction product of the enzyme and the detection reagent may be detectable. When the enzyme is alkaline phosphatase or horseradish peroxidase, the reaction product may be a chromophore. When the enzyme is a luciferase the reaction product may be photons of light. Other enzymes, known to those skilled in the art, may be used as detectable moieties. Such enzymes are known to those skilled in the art and may be substituted without deviating from the spirit of the invention. Alternative embodiments wherein the detectable moiety is directly attached to the first antibody are within the scope of the invention.

After detecting the presence of the first antibody, the ligase reaction and the detection of a DNA probe molecule are performed as described above may be labeled with a fluorescent dye, and the antibody molecule may be labeled with a different fluorescent dye. The dyes may be selected so that they permit simultaneous detection. The solution containing the DNA probe and the antibody molecule may optionally include blocking agents. Blocking agents used as blocking agents include BSA, dry milk, detergents, and the like. After completion of the reaction, the tissue sample is washed with a buffered solution and examined under a fluorescent microscope. More than one protein molecule can be simultaneously detected. This is accomplished by using antibodies specific for each protein of interest and is limited only by the number of fluorescent dyes that can be simultaneously visualized.

Example 10

Simultaneous Detection of 3' Overhangs and RNA Molecules

The present invention permits the detection of RNA molecules in cells undergoing apoptosis. Tissue samples are prepared for ligation as described above. The sample is hybridized with an oligonucleotide complementary to the sequence of an RNA molecule of interest. The exact conditions are hybridization are dependent upon the sequence of interest and the length of the oligonucleotide probe. Appropriate methodology for selection of hybridization conditions is contained in Sambrook, et al. Hybridization may be conducted at a temperature from about room temperature to about 74° C. for a period of time from about 15 minutes to 48 hours. Preferably, hybridization may be conducted for a period of time from about 4 hours to about 16 hours, at a temperature from about 40° C. to about 65° C. After hybridization, the sample may be washed. The stringency of the wash conditions, i.e., ionic strength and temperature, are adjusted according to the length of the probe and nucleotide sequence of the probe. After an appropriate period of washing, the sample is contacted with a solution containing a DNA molecule capable of being ligated to a 3'-overhang, a DNA ligase enzyme, and the appropriate co-factors. Ligation reaction is conducted at room temperature for about 1 hour. The sample is then washed and the presence of the oligonucleotide and the DNA molecule are detected. The presence of the oligonucleotide and the DNA molecule in the same cell indicate that the RNA molecule of interest is present in apoptotic cells.

The above assay may be configured in a variety of ways. The oligonucleotide used may be an RNA molecule or a DNA molecule. Detectable moieties may be incorporated into the oligonucleotide. These moieties may be enzymes, small molecules, chromophores, fluorophores or radio-labeled molecules. In a preferred embodiment, the detectable moiety is FITC. Other fluorophores known to those skilled in the art are within the scope of the invention.

Detectable moieties may be incorporated into the DNA molecule to be ligated. For example, the detectable molecules may be enzymes, small molecules, fluorophores, chromophores and radio-labeled molecules. In a preferred embodiment, both the oligonucleotide and the DNA molecule to be ligated incorporate fluorophores. In this embodiment, the fluorophore incorporated in the oligonucleotide fluoresces at a wavelength different from that at which the fluorophore incorporated into the DNA fluoresces. This permits the simultaneous detection of the oligonucleotide and DNA molecule. The DNA molecule that is ligated to the 3'-overhangs in the DNA of the apoptotic cell may contain a small molecule such as biotin, bromine or digoxigenin. After ligation, the sample is contacted with a molecule which binds to the small molecule, such as an avidin or streptavidin when the small molecule is biotin, or anti-digoxigenin antibody or antibody fragment. The molecule that binds to the small molecule is conjugated to a detectable moiety. The detectable moiety may be an enzyme, fluorophore, chromophore or radio-labeled molecule.

Example 11

Solid Support Capture Assay

The present invention may be used to detect and/or isolate DNA target molecules having defined overhanging termini. This is accomplished by attaching a nucleic acid probe molecule having a defined terminus to a solid support. The solid support may be any solid support known in the art including, but not limited to, membranes, microtiter plates, agarose beads, beads made of a synthetic resin, and any other solid support known in the art. In a preferred embodiment, the solid support will be a paramagnetic particle coated with a synthetic resin. This embodiment allows facile separation of the beads from the reaction solution.

The nucleic acid probe molecule attached to the solid support is called the capturing fragment. The capturing fragment is selected so as to have a complementary terminus to the defined overhanging terminus of the DNA target molecule. The fragment may be prepared by any means known in the art. For example, the fragment may be prepared from a larger DNA molecule by treatment of the larger molecule with a nuclease that generates the desired overhanging termini. The DNA fragments possessing the desired overhanging termini may then be isolated and subsequently fixed to the solid support, using any methodology known in the art. For example, the solid support may be provided with a reactive functionality that is capable of reacting with functional groups present in the capturing fragment. Alternatively, the capturing fragment may be modified so as to contain a reactive functionality capable of reacting with the solid support. In other embodiments, the capturing fragment will be provided with a small molecule that can be bound by a group present on the solid support. For example, the capturing fragment may be provided with a biotin moiety or a digoxigenin and the solid support with streptavidin or an anti-digoxigenin antibody. Those skilled in the art will readily appreciate that any methodology that does not affect the overhanging terminus of the capture fragment may be used to fix the capture fragment to the solid support.

The capture fragment may be designed so as to contain additional desirable structural characteristics beyond an overhanging terminus. For example, the capturing fragment may be equipped with a restriction enzyme site. After the capturing fragment has been used to isolate the corresponding nuclease-cleaved DNA, the capturing fragment may be cleaved using a restriction endonuclease, thereby liberating a DNA molecule that includes a portion of the capturing fragment in addition to the nuclease cleaved fragment.

The DNA target molecule can be cloned and sequenced using methodologies well known to those skilled in the art. For example, the nuclease-cleaved DNA can be ligated to the capturing fragment. Subsequently, the solid support may be treated with Pfu polymerase to generate blunt ended fragments attached to the solid support. The solid support may then be treated with a restriction enzyme to cleave the blunt ended fragment from the solid support. The fragment can then be cloned into a vector treated so as to have a blunt end and an end that corresponds to the end generated by the restriction enzyme. Those skilled in the art can readily envision other, equivalent cloning strategies. Alternatively, the capturing fragment may be equipped with a sequence to which a PCR primer will bind. After reaction with the nuclease cleaved DNA, the reaction mixture may be provided with the necessary reagents to perform PCR on the captured nuclease cleaved fragment. It is readily apparent to those skilled in the art that more than one desirable functional characteristics can be incorporated into the capturing fragment. For example, both restriction enzyme cleavage sites and PCR primer binding sites may be incorporated into the same capturing fragment.

The capturing fragment may be provided with a detectable moiety. After ligating the nuclease cleaved DNA to the capturing fragment, the capturing fragment may be cleaved from the solid support and the presence of the detectable moiety assayed. It may be necessary to perform a step of isolating capture fragment bound to nuclease cleaved DNA from capture fragment not so bound. Those skilled in the art can readily accomplish this using known methods based upon the difference in size of the two types of fragment.

The DNA suspected of containing nuclease-cleaved ends may be isolated from any source. The DNA is isolated using methodologies readily known by those skilled in the art. After the DNA suspected of containing nuclease cleaved ends is isolated, it is combined with capturing fragment in the presence of DNA ligase and the requisite co-factors, such as divalent metal ions and ATP. After a suitable length incubation, the ligating solution is removed by washing and the presence or absence of nuclease-cleaved DNA can be detected. The basic assay described above can be configured in a variety of ways. For example, the capturing fragment may be provided to the ligation solution as a fragment free in solution. In embodiments of this nature, the capturing fragment will be provided with a binding moiety, such as biotin or digoxigenin. After a suitable reaction period, a solid support containing a molecule capable of attaching to the binding moiety, such as avidin, streptavidin, or anti-digoxigenin, is mixed with the solution. After an incubation period to allow the binding moiety to be attached to the solid support, the solid support can be washed so as to remove unbound material and then treated in any fashion desirable.

Alternatively, the capturing fragment may be provided to the ligation mixture already attached to a solid support. After the ligation reaction is allowed to proceed, the solid support can then be washed as before.

The present invention may be used as an assay to detect termini of a specific overhang present in a DNA sample. After the ligation and attachment to solid support as described above, the sample is washed and then provided with a known quantity of complementary termini. The fragments containing these complementary termini will be detectable in some fashion, for example, as radio labeled or fluorophore or chromophore containing. A second ligation reaction may be performed so as to attach the radio labeled fragments to any remaining overhanging termini that have not bound nuclease treated DNA from the ligation reaction. The more radio labeled material that binds, the fewer correct overhanging termini were present in the original sample.

Example 12

Double Labelling of DNA Strand Breaks with Hairpin Oligonucleotides and Terminal Transferase To test the sensitivity and specificity of the oligonucleotide hairpin probes in labelling double-strand breaks in nuclei of apoptotic cells, we applied probes to sections taken from tissues in which apoptotic cells were present, but which might also include cells undergoing necrosis, which may have single-strand breaks. The tissues used were: thymus from rats treated with dexamethasone; mouse kidney in which apoptosis was provoked by puncturing the capsule; and Wilms tumor containing extensive areas of necrosis. A double-staining procedure was used enabling the sequential ligation of a hairpin oligonucleotide probe followed by the labelling of all available 3'-hydroxyl DNA ends, in double and single strand breaks, by terminal transferase. The detectable moiety on the oligonucleotide probe, biotin, was visualized with an fluorescein-avidin conjugate, and 3'-hydroxyl ends were visualized by addition of Texas red-dUTP. The following experiments used a hairpin probe with a single 3'-A overhang (FIG. 8).

Both forms of labelling were dependent on the presence of enzyme (ligase or terminal transferase); no nuclear signal was observed when enzymes were omitted from the reaction mix added to the sections. Apoptotic cells were specifically labeled with equal intensity by both techniques.

The relative specificity of the labelling techniques for strand breaks in apoptotic and necrotic cell nuclei was tested by comparison of samples from dexamethasone-treated rat thymus, a tissue with large numbers of apoptotic cells, and a sample of Wilms' tumor with extensive necrosis. In the thymus, most cells undergoing apoptosis were labelled by both techniques, although a few appeared to be selectively labelled by terminal transferase or by ligation of hairpin probe. In the necrotic areas of the tumor, some cells were labelled by ligation of the hairpin probe. However, these cells were surrounded by much larger numbers of cells which were labelled to varying extents by terminal transferase. These cells appeared to be undergoing necrosis when these areas of the tumor were examined by conventional histology. The difference between the thymus and Wilms' tumor specimens was most evident when both fluorochromes were observed simultaneously with a dual-wavelength filter. Whereas most cells in the thymus appeared yellow, indicating equal labeling by both techniques, few cells in the tumor appeared yellow, indicating much greater labeling by terminal transferase than by ligation of hairpin probes.

Interestingly, observation of double-stained apoptotic cells by confocal microscopy revealed intranuclear patterns of labelling by the hairpin probe. Some cells had chromatin condensations or marginations that were equally labelled by hairpin probes and by terminal transferase; however, many cells in the thymus showed a zone of more intense double-strand break labeling around the periphery of the nucleus, whereas terminal transferase labeled these nuclei more uniformly.

Example 13

Different Types of Probes

Three types of probes blunt, single-nucleotide and double-nucleotide overhangs were compared for their specificity and sensitivity. The patterns of labelling for the three kinds of probes were generally similar. However, the NN overhang probe produced a more intense signal but also showed more background (i.e., signal in the absence of enzyme) than the other probes. Additionally, necrotic areas of the tumor were more intensely labelled by both the NN and blunt-ended probes than by the single A overhang.

The single-strand A overhang probe appears to have the best specificity for labelling apoptotic cells. The likely mechanism for the production of double-strand breaks with 3'-overhangs in apoptotic cells has been previously discussed. Although breaks with double-nucleotide overhangs may be frequent, better methods for the suppression of nonspecific binding of probes with double-nucleotide overhangs will be required to reliably detect breaks with overhangs of two and, presumably, greater numbers of nucleotides.

The methodology could be extended by the design of hairpins with 5'-overhangs to enable detection of 5'-overhang strand breaks. However, in this case binding to single-stranded DNA fragments will occur because the recessed 3'-hydroxyl on the oligonucleotide would bind to 5'-phosphates on the section, which could be at the end of a single-stranded DNA fragment as well as a double-strand break with a 5'-overhang. Thus the detection of 5'-overhangs would require dephosphorylation of the tissue section before ligation and the use of a 5'-phosphorylated oligonucleotide.

The ease of synthesis of hairpin oligonucleotide probes and the simple procedure for the detection of double-strand breaks should enable this methodology to have wide application in staining of apoptotic cells, with potential extension to the detection of different kinds of double-strand breaks in dying cells, which may have mechanistic and diagnostic significance.

Example 14

Simultaneous Labelling by Ligation and Prior Art Methods

In one embodiment of the present invention, a sample is simultaneously probed using the ligation based methodology disclosed in the instant application in combination with those methodologies of the prior art used for detection of apoptotic cells. The prior art methods preferred are the assay based upon the use of terminal deoxynucleotidyl transferase (TdT) mediated biotinylated dUTP nick end labeling (TUNEL) and the assay based upon the use of the Klenow fragment to fill in gaps in DNA. The ligation reaction may be performed at the same time as the TdT or Klenow reaction. In other embodiments, the reactions may performed sequentially either with the ligation reaction being performed first or with the prior art reaction being performed first.

This embodiment of the invention will permit the simultaneous detection of free hydroxyls, detected by the prior art methods, and ligatable overhang structures, detected with the methods of the present invention.

This invention has been described in terms of specific embodiments set forth in detail, but it should be understood that these are by way of illustration only and that the invention is not limited to the specifically recited embodiments. Modifications and alterations will be readily apparent to those skilled in the art and these modifications and alterations are within the scope of the invention. Accordingly, these modifications and alterations of the disclosed invention are considered to be within the scope of the invention and the following claims.

What is claimed is:

1. A method for detecting apoptotic cells in a sample, comprising the steps of:
   fixing a sample, the sample containing DNA, the DNA having an end characteristic of apoptosis;
   contacting the sample with a solution containing a nucleic acid molecule and a nucleic acid ligase enzyme, the nucleic acid molecule being ligatable to the DNA end characteristic of apoptosis; and
   detecting the nucleic acid molecule, wherein the detection of the nucleic acid molecule correlates to the presence of apoptotic cells.

2. A method according to claim 1, wherein the sample is a tissue sample.

3. A method according to claim 1, wherein the nucleic acid molecule comprises a detectable moiety.

4. A method according to claim 3, wherein the detectable moiety is selected from the group consisting of, enzymes, small molecules, chromophores, fluorophores and radio-labeled materials.

5. A method according to claim 1, further comprising the steps of:
   contacting the tissue sample with a solution containing a protease; and
   washing the tissue sample to remove the protease.

6. A method according to claim 3, wherein the detecting step is performed using a reagent comprising an enzyme.

7. A method according to claim 3, wherein the detecting step is performed using a reagent comprising an antibody or fragment thereof that binds to the detectable moiety.

8. A method according to claim 3, further comprising the steps of:
   contacting the tissue sample with a reagent that comprises a first molecule that binds to the detectable moiety; and
   subsequently contacting the tissue sample with a reagent that comprises a second molecule that binds to the first molecule.

9. A method according to claim 8, wherein the first molecule is selected from the group consisting of antibodies, fragments of antibodies, avidin and streptavidin.

10. A method according to claim 3, further comprising the step of:
    contacting the tissue sample with a reagent that comprises a molecule having a first portion that binds to the detectable moiety and a second portion that comprises an enzyme.

11. A method according to claim 10, wherein the first portion is selected from the group consisting of antibodies, fragments of antibodies, avidin and streptavidin.

12. A method according to claim 10, wherein the second portion comprises an enzyme selected from the group consisting of phosphatases, galactosidases, glucuronidases, peroxidases and luciferases.

13. A method according to claim 10, wherein the first portion comprises streptavidin and the second portion comprises an enzyme selected from the group consisting of phosphatases, galactosidases, glucuronidases, peroxidases, and luciferases.

14. A method according to claim 1, wherein the nucleic acid has a blunt end.

15. A method according to claim 1, wherein the nucleic acid has a 3'-overhang.

16. A method of detecting apoptotic cells in a sample, comprising the steps of:
    isolating DNA from the sample, the DNA having an end characteristic of apoptosis;
    fractionating the DNA by size;
    transferring the DNA to a solid support;
    contacting the solid support with a solution containing a nucleic acid probe molecule and a nucleic acid ligase enzyme, the nucleic acid molecule being ligatable to the DNA end characteristic of apoptosis; and
    detecting the nucleic acid probe molecule, wherein the detection of the nucleic acid probe molecule correlates to the presence of apoptotic cells.

17. A method according to claim 16, wherein the nucleic acid probe molecule comprises a detectable moiety.

18. A method according to claim 17, wherein the detectable moiety is selected from the group consisting of enzymes, small molecules, chromophores, fluorophores, and radio-labeled materials.

19. A kit for the detection of apoptotic cells, comprising:
    a nucleic acid probe which ligates specifically to the DNA of cells that have undergone apoptosis, said nucleic acid probe comprising a detectable moiety;
    an enzyme for ligating said nucleic acid probe; and
    reagents for detecting the detectable moiety.

20. A kit according to claim 19, wherein the nucleic acid probe has a blunt end.

21. A kit according to claim 19, wherein the nucleic acid probe has a 3'-overhang.

22. A kit according to claim 20, wherein said nucleic acid probe is attached to a solid support.

23. A kit according to claim 21, wherein said nucleic acid probe is attached to a solid support.

24. A method for detecting the presence of apoptotic cells in a sample, comprising the steps of:
    isolating DNA from a sample, the DNA having an end characteristic of apoptosis;
    fixing a nucleic acid molecule to a solid support, the nucleic acid molecule being ligatable to the DNA;
    ligating the DNA to the nucleic acid molecule; and
    detecting the ligation of the DNA to the nucleic acid, wherein the ligation of DNA to nucleic acid correlates to the presence of apoptotic cells in the sample.

25. A method according to claim 24, wherein the nucleic acid molecule includes a nucleotide sequence that serves as a recognition site for a restriction endonuclease.

26. A method according to claim 24, wherein the nucleic acid molecule is cleavably fixed to the solid support.

27. A method according to claim 24, wherein the nucleic acid molecule has a blunt end.

28. A method according to claim 24, wherein the nucleic acid molecule has a 3'-overhang.

29. A method for detecting apoptotic cells in a sample, comprising the steps of:

isolating DNA from a sample, the DNA having an end characteristic of apoptosis;

fixing the DNA to a solid support;

contacting the solid support with a solution containing a nucleic acid molecule and a nucleic acid ligase enzyme, the nucleic acid molecule being ligatable to the DNA; and detecting the presence of the nucleic acid molecule, wherein the presence of the nucleic acid molecule correlates to the presence of apoptotic cells in the sample.

30. A method according to claim 29, wherein the nucleic acid molecule has a blunt end.

31. A method according to claim 29, wherein the nucleic acid molecule has a 3'-overhang.

32. A method for detecting apoptotic cells in a sample, comprising the steps of:

fixing a sample, the sample containing DNA;

contacting the sample with a solution containing a nucleic acid probe which ligates specifically to the DNA of cells that have undergone apoptosis, the nucleic acid probe comprising a detectable moiety, the solution further comprising an enzyme for ligating the nucleic acid probe; and detecting the nucleic acid probe, wherein the detection of the nucleic acid probe correlates to the presence of apoptotic cells.

33. A method of detecting apoptotic cells in a sample, comprising the steps of:

isolating DNA from the sample;

fractionating the DNA by size;

contacting the DNA with a solution containing a nucleic acid probe which ligates specifically to the DNA of cells that have undergone apoptosis, the nucleic acid probe comprising a detectable moiety, the solution further comprising an enzyme for ligating the nucleic acid probe; and detecting the nucleic acid probe molecule, wherein the detection of the nucleic acid probe molecule correlates to the presence of apoptotic cells.

* * * * *